(12) United States Patent
Hehli et al.

(10) Patent No.: US 7,025,151 B2
(45) Date of Patent: Apr. 11, 2006

(54) DEVICE FOR LIMITING A TORQUE TO BE TRANSFERRED

(75) Inventors: Markus Hehli, Davos (CH); Beat Knuchel, Grenchen (CH); Rolf Schneider, Biel (CH)

(73) Assignee: Synthes (USA), West Chester, PA (US)

( * ) Notice: Subject to any disclaimer, the term of this patent is extended or adjusted under 35 U.S.C. 154(b) by 82 days.

(21) Appl. No.: 10/785,795

(22) Filed: Feb. 23, 2004

(65) Prior Publication Data
US 2005/0145402 A1 Jul. 7, 2005

Related U.S. Application Data

(63) Continuation of application No. PCT/CH01/00517, filed on Aug. 23, 2001.

(51) Int. Cl.
*A61B 17/88* (2006.01)
*B25B 23/14* (2006.01)

(52) U.S. Cl. ............ 173/176; 173/178; 173/93.5; 173/205; 81/475; 192/54.5

(58) Field of Classification Search ............ 173/176, 173/2, 5, 13, 178, 93.5, 93, 122, 205; 81/475, 81/467, 477; 192/54.1, 54.5
See application file for complete search history.

(56) References Cited

U.S. PATENT DOCUMENTS

| | | | |
|---|---|---|---|
| 2,227,627 A | | 1/1941 | Bruzon |
| 2,351,996 A | * | 6/1944 | Morgan ............... 192/54.5 |
| 3,855,662 A | * | 12/1974 | Fortin ............... 15/250.01 |
| 3,942,337 A | * | 3/1976 | Leonard et al. ......... 464/36 |
| 4,272,973 A | * | 6/1981 | Fu-Tsai ............... 81/475 |
| 4,517,865 A | | 5/1985 | Huang |
| 4,809,572 A | * | 3/1989 | Sasaki ............... 81/429 |
| 6,132,435 A | | 10/2000 | Young |
| 6,487,943 B1 | * | 12/2002 | Jansson et al. ......... 81/475 |
| 6,834,889 B1 | * | 12/2004 | Sunde et al. .......... 285/92 |

FOREIGN PATENT DOCUMENTS

| | | |
|---|---|---|
| CH | 540 094 A | 8/1973 |
| DE | 79 03 812 U1 | 5/1979 |
| DE | 35 39 502 C1 | 2/1987 |
| EP | 0 174 276 A1 | 3/1986 |
| EP | 1 092 510 A2 | 4/2001 |
| EP | 1 110 512 A1 | 6/2001 |
| EP | 1 092 510 A3 | 7/2002 |
| FR | 1 051 913 | 1/1954 |
| FR | 2 758 287 A1 | 7/1998 |
| WO | WO 99 52684 | 10/1999 |

* cited by examiner

*Primary Examiner*—Scott A. Smith
(74) *Attorney, Agent, or Firm*—Jones Day

(57) ABSTRACT

The invention relates to a device for limiting torque to be transferred, having first and second shafts having a longitudinal axis; at least first and second transfer elements arranged coaxial with the longitudinal axis of the first and second shafts, the first transfer element associated with the first shaft and the second transfer element associated with the second shaft; the two transfer elements having substantially complementary engaging faces; at least one elastic element configured to bias the engaging faces of the first and second transfer elements into engagement with each other; wherein an engaging face of the first transfer element has a first engageable contour, and an engaging face of the second transfer element has a second engageable contour, wherein first and second engageable contours each have first and second active angles and a first passive angle.

22 Claims, 4 Drawing Sheets

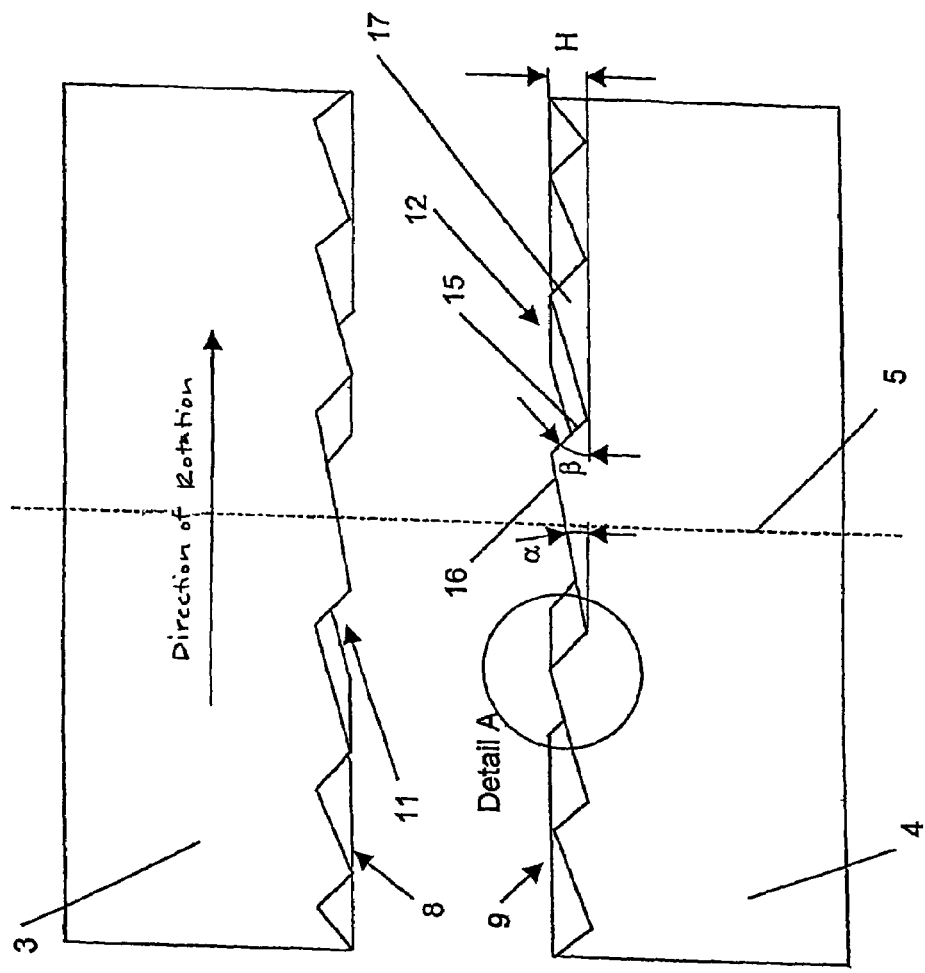
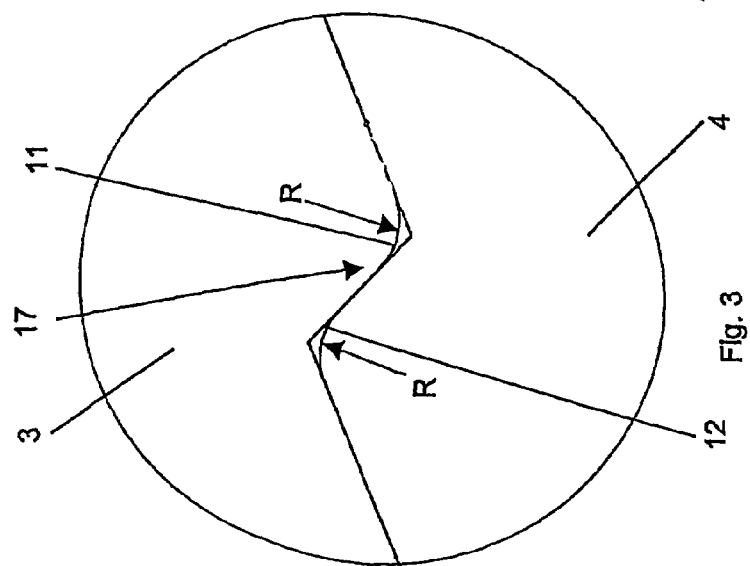
Fig. 2
Fig. 3

DEVICE FOR LIMITING A TORQUE TO BE TRANSFERRED

CROSS-REFERENCE TO RELATED APPLICATIONS

This application is a continuation of International Application No. PCT/CH01/00517, filed on Aug. 23, 2001.

FIELD OF THE INVENTION

The invention relates to a device for limiting a torque, which is to be transferred.

BACKGROUND OF THE INVENTION

In the case of osteosynthetic treatments of fractures or the implantation of artificial joints, implants, such as bone plates or implant parts, are frequently fixed in a position at the bone by means of bone screws. Such bone screws frequently are self-drilling and self-cutting, and are screwed with a drill or a similar device into the bone. In so doing, the maximum torque, which is exerted on the bone screw and, accordingly, on the threaded connection between the bone screw and the bone, is to be limited to a particular value.

A device for limiting the maximum torque, which can be applied on a screw during a surgical intervention, is described in U.S. Pat. No. 6,132,435 to YOUNG. This known device comprises a driving shaft, which contains a disk-shaped segment with boreholes, disposed on a circle concentric with the axis of rotation, for accommodating balls, a driving shaft segment, which also contains a disk-shaped segment with spherical-shaped depressions, disposed complementary to the boreholes, and a housing, in which the driving shaft and the driving shaft segment are mounted. The balls are pressed by means of springs into the depressions in the disk-shaped segment of the driving shaft segment, the force of the springs being adjustable by means of loosening or tightening a threaded connection between the disk-shaped segment at the driving shaft and the housing.

It is a disadvantage of this known device that the same maximum torque is transferred in both directions of rotation. This is disadvantageous in surgical technique if a bone screw has become ingrown and, as a result, the torque for loosening it during removal has increased.

The invention is to provide a remedy here. It is an object of the invention to provide a device, which permits the transfer of a maximum torque, once set, only in a desired direction of rotation, while in the other direction of rotation, for example, for loosening screws, the torque, which can be transferred, may be larger or smaller.

SUMMARY OF THE INVENTION

The inventive device comprises first and second shafts having a longitudinal axis; at least first and second transfer elements arranged coaxial with the longitudinal axis of the first and second shafts, the two transfer elements having substantially complementary engaging faces; and at least one elastic element configured to bias the engaging faces of the first and second transfer elements into engagement with each other. The first transfer element may be associated with the first shaft, and the second transfer element may be associated with the second shaft.

In one embodiment, each engaging face of the first and second transfer elements may have at least one engageable contour, each contour having a first and second active angle and a first passive angle. The first and second active angles of at least one engageable contour may be substantially unequal.

In another embodiment, each engaging face of the first and second transfer elements may have at least one engageable contours, each contour having a first active angle and a first passive angle. The first active angle and first passive angle of at least one engageable contour may be substantially unequal.

In yet another embodiment, each engaging face of the first and second transfer elements may have at least one engageable contours, each contour having a first and second active angle and a first and second passive angle. The first and second active angles of at least one engageable contour may be substantially unequal. The first and second passive angles of at least one engageable contour may be substantially unequal.

The slopes of the teeth of the two contours, which may be passive during the transfer of torque in the desired direction of rotation, may enclose an angle $\beta$, which may be between 45° and 90°, with the diameter of the transfer elements, which may be perpendicular to the longitudinal axis. The angle $\beta$ selected affects the maximum torque to be transferred (the loosening torque at $\beta=90°$ is infinite) at a particular contacting force of the transfer elements. The slopes of the teeth of the two contours, which may be active during the transfer of torque in the desired direction of rotation, may enclose an angle $\alpha$, which may be between 1° and 45°, with the diameter of the transfer elements, which may be perpendicular to the longitudinal axis.

In a different embodiment of the inventive device, the slopes of the teeth may be configured so that the angle $\alpha_A$ at the external diameter of the contours and the angle $\alpha_I$ at the internal diameter of the contours are unequal in size. As a result, there may be a linear contact over the whole width of the contours and there may be no point stress, which could have a negative effect on the device, especially on the wear properties.

In a further embodiment, the teeth of the two contours may be rounded off as they terminate in the respective end surface. The radii of these roundings-off may be between 0.1 mm and 1.0 mm. The wear behavior may be optimized by the choice of this radius.

Further advantageous embodiments of the invention are characterized in the dependent claims.

The advantages, achieved by the invention, are to be seen essentially therein that, due to the inventive device, a transfer of torque with a particular, maximum transferable torque may be enabled in only one direction of rotation, whereas the maximum transferable torque may assume a different value in the other direction of rotation.

BRIEF DESCRIPTION OF THE DRAWINGS

Numerous features of the present invention are disclosed in the accompanying drawings, wherein similar reference characters denote similar elements throughout the several views, and wherein:

FIG. 2 is a side view of the transfer elements of the inventive device.

FIG. 3 is a detail view of the contours of transfer elements of FIG. 2.

DETAILED DESCRIPTION OF THE PREFERRED EMBODIMENTS

Figure 1:
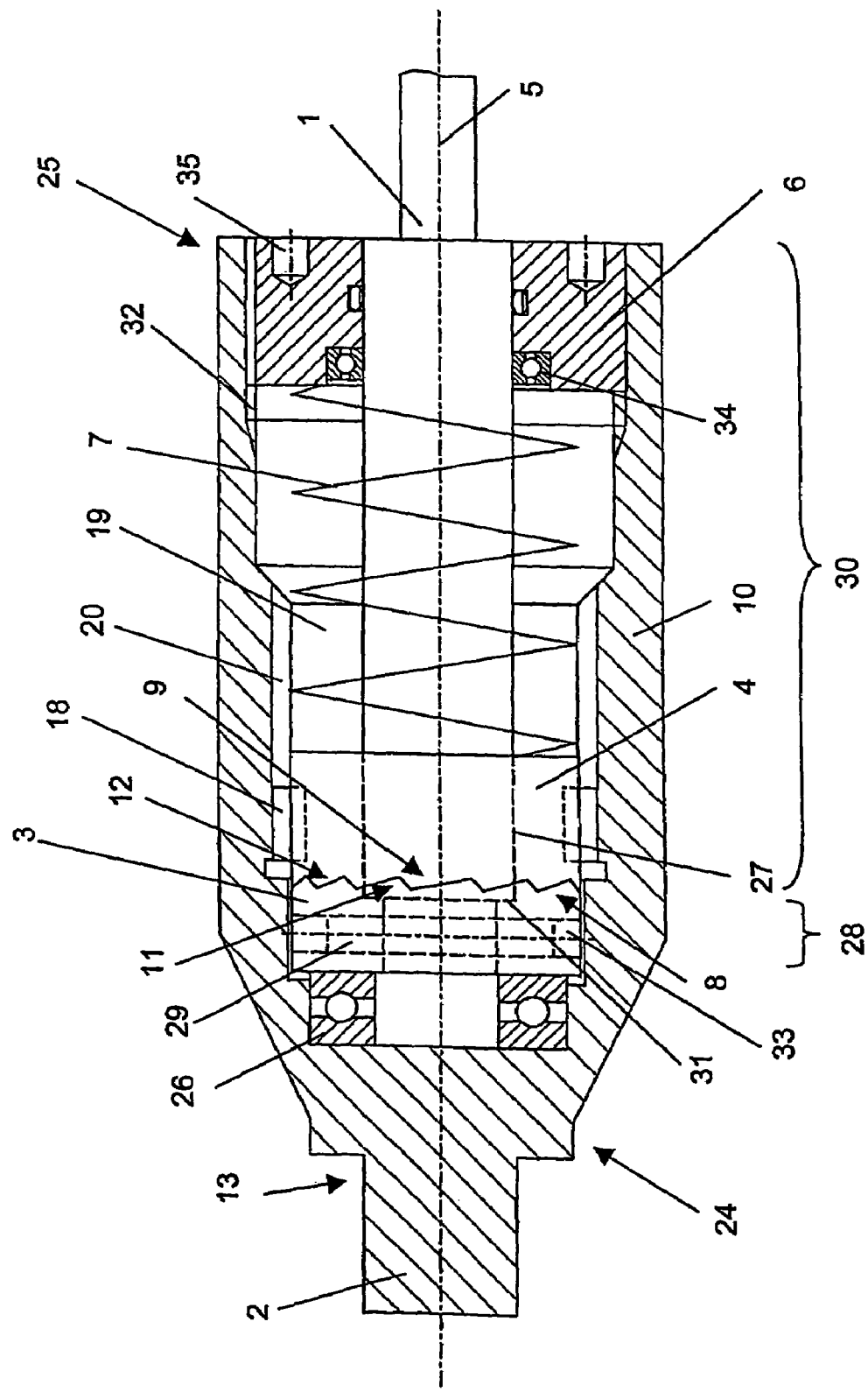
FIG. 1 is a longitudinal cross-sectional view of the inventive device.

In FIG. 1, an embodiment of the inventive device is shown, which may permit a transfer of torque between a first shaft 1 and a second shaft 2. The two shafts 1, 2 may be disposed coaxially, sharing a longitudinal axis 5. The two shafts 1, 2 may also be coupled directly or indirectly with one of the transfer elements 3, 4. The transfer of torque may take place over the mutually complementary contours 11, 12 mounted at mutually opposite end faces 8,9 of the transfer elements 3,4. A first transfer element 3 may be mounted in the housing 10, so that it may rotate about the longitudinal axis 5, whereas a second transfer element 4 may be rotatably attached with the housing 10. The front end 13 of the second shaft 2 may be fastened to the second end 24 of the housing 10.

The housing 10 may have a hollow space 19, which may be coaxial with the longitudinal axis 5, a first end 25 and a second end 24. The second end 24 may adjoin the second shaft 2. The hollow space 19 may be open at the first end 25 of the housing 10, so that the transfer elements 3,4 may be disposed in the hollow space 19. An axial bearing 26, which may be contacted, axially adjoining, by a first transfer element 3, may be disposed in the hollow space 19 at the second end 24 of the housing 10.

A borehole 27 may be drilled concentrically through each of the transfer elements 3,4. The diameter of the borehole 27 in a second transfer element 4 may be larger than the diameter in a first transfer element 3, so that the front segment 28 of the first shaft 1 may be passed through the second transfer element 4 and subsequently may be connected axially and detachably with the first transfer element 3 at the second end 24 of the housing 10. This may be achieved, for example, by means of a pin 29, which may be inserted in a transverse borehole 33 perpendicular to the longitudinal axis 5 through the front segment 28 of the shaft 1 and the first transfer element 3. The second transfer element 4 may be mounted axially and may be rotationally movable on the middle segment 30 of the first shaft 1, so that the end face 8 of the first transfer element 3 may lie opposite to the end face 9 of the second transfer element 4 and the contours 11,12, disposed at the end faces 8,9 may engage one another.

The middle segment 30 of the first shaft 1 may have a larger diameter than the front segment 28, so that a shoulder 31 may be formed at the first shaft 1 between the front and middle segment 30. The shoulder 31 may also contact the first transfer element 3. Therefore, the first shaft 1 may be held axially by the first transfer element 3, while the transfer of torque may be brought about by the pin 29. The transfer of torque between the housing 10, which may be firmly connected with the second shaft 2, and the second transfer element 4, may take place over sliding blocks 18. The sliding blocks 18 may be mounted peripherally at the second transfer element 4, and may be axially disposed in the housing 10 in grooves 20 parallel to the longitudinal axis 5.

The second transfer element 4 may be pressed axially against the first transfer element 3 by elastic means 7, which may be constructed in the embodiment shown here as a compression spring disposed coaxially with the longitudinal axis 5. The elastic means 7 may be clamped axially between the second transfer element 4 and tensioning means 6, the tensioning means 6 in this embodiment consisting of a screw. The screw may be screwed into a complementary inner thread 32 at the first end 25 of the housing 10. The tensioning means 6 may also be disposed concentrically to the longitudinal axis 5, and a hole may be drilled through them coaxially, so that the middle segment 30 of the first shaft 1 may be passed through the tensioning means 6. The middle segment 30 of the first shaft 1 may be mounted radially in the tensioning means 6 by means of a radial bearing 34, which may be constructed, for example, as a ball bearing. The contacting force of the elastic means 7 may be adjusted by its pre-tension, and the pre-tension may be adjusted by axially turning the clamping means 6 in or out in the hollow space 19 of the housing 10. The tensioning means 6 may be operated at the first end 25 of the housing 6, with depressions 35 for accommodating a screwdriver.

In FIG. 2, transfer elements 3,4 of an embodiment of the inventive device are shown. The contours 11,12 at the transfer elements 3,4 may be constructed asymmetrically. The active slopes of the teeth 16 of the two contours 11,12 may enclose an angle $\alpha$ with the diameter of the transfer elements 3, 4, which is approximately 20° in the and which may be is perpendicular to the longitudinal axis 5. The passive slopes 15 of the teeth may enclose an angle $\beta$, which is approximately 45° in the embodiment shown here, with the diameter of the transfer elements 3,4.

FIG. 3 shows enlargement of the contours 11,12, as shown in FIG. 2. The tips of the teeth 17 in this embodiment are rounded off with a radius R.

Figure 4:
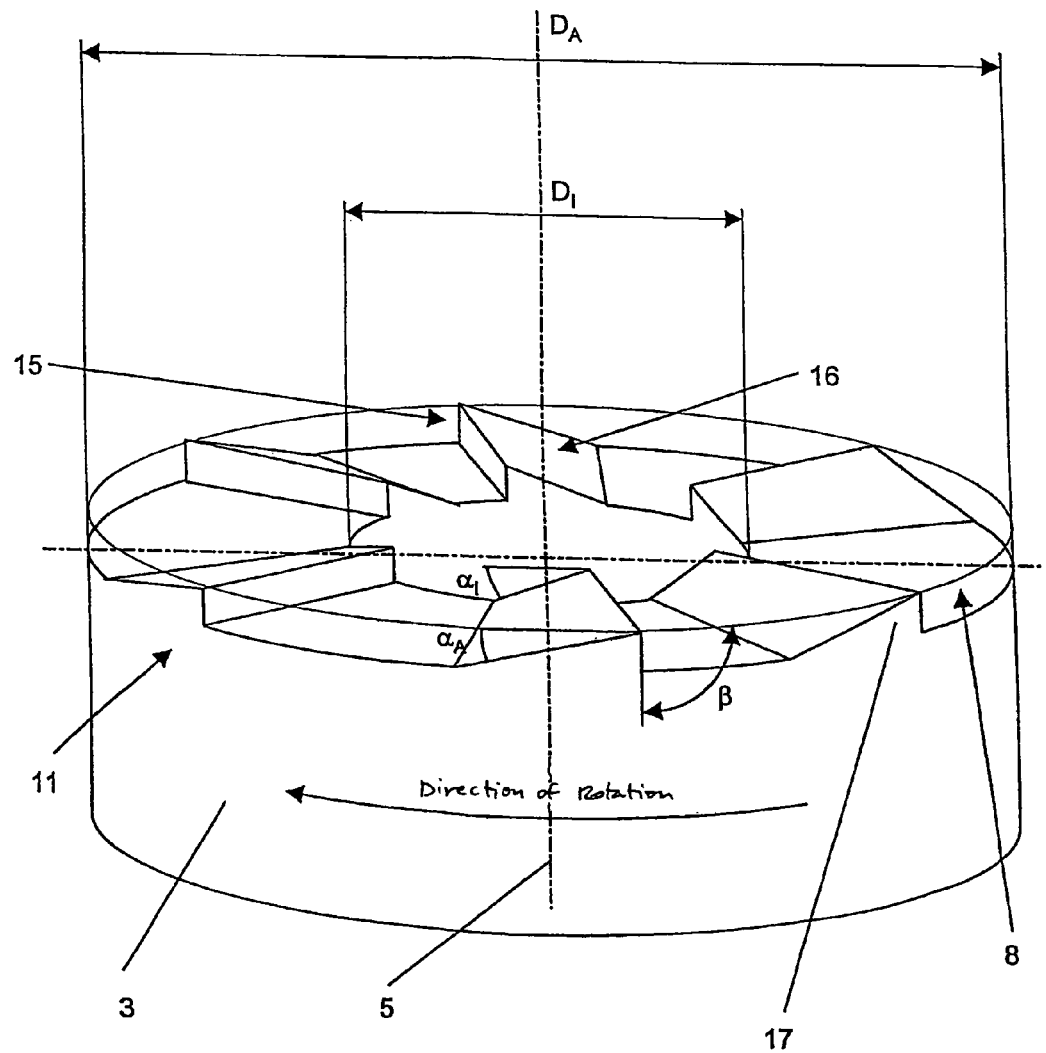
FIG. 4 is a perspective view of a transfer element in an alternative embodiment of the inventive device.

An alternative embodiment of a transfer element is shown in FIG. 4. The tips of the teeth of the contours 11 may rest on the circular end surface 8 of a first transfer element 3. This circular end surface 8 may have an outer diameter $D_A$ and an inner diameter $D_I$. The teeth 17 may be constructed asymmetrically. The slopes 16 of the teeth, which may be active in the desired direction of rotation for transferring torque, may have a varying angle $\alpha$ between the outer diameter $D_A$ and the inner diameter $D_I$ of the end surface 8. The angle $\alpha_A$ at the outer diameter $D_A$ may be smaller than the angle $\alpha_I$ at the inner diameter $D_I$. The slopes 15 of the teeth, which may be passive in the desired direction of rotation, may enclose an angle $\beta$ of 90° with the end surface 8. The contours 12 at a second transfer element 4 (not shown) may be complementary to the contours 11 at the first transfer element 3. The tips of the teeth 17 may also be rounded off, as shown in FIG. 3.

Figure 5:
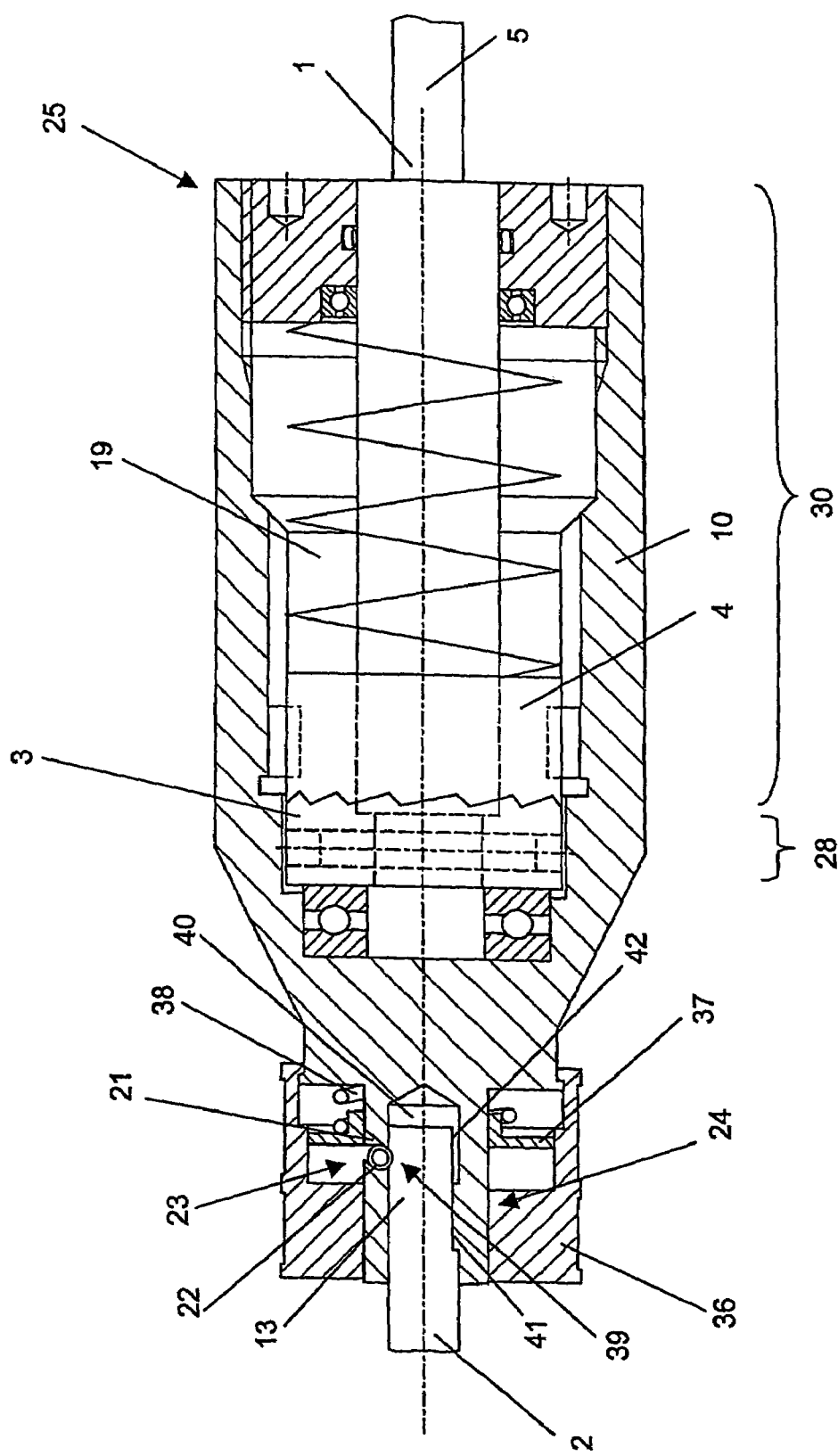
FIG. 5 is a longitudinal cross-sectional view of an alternative embodiment of the inventive device.

An alternative embodiment of the inventive device shown in FIG. 5, comprises a driving first shaft 1, which may be firmly connected with a first transfer element 3. As compared to the embodiment shown in FIG. 1, the first shaft 1 has a different second end 24 of the housing 10, where the torque applied by the first shaft 1 may be transferred to a second shaft 2 and a tool or instrument (not shown). The second shaft 2 may be fastened detachably to the second end 24 of the housing 10 by means of a locking mechanism 23. The locking mechanism 23 may be constructed of a slide block. The locking mechanism 23 may be operated by means of an operating handle 36, which, axially displaceable with respect to the longitudinal axis 5, may be connected with the second end 24 of the housing 10. A bolt 22, which may be movable perpendicularly to the longitudinal axis 5, may be fastened in the operating handle 36 perpendicularly to the longitudinal axis 5. Furthermore, the bolt 22, which also may be movable in a notch 21 extending at an angle to the longitudinal axis 5, may be connected with the second end 24 of the housing 10. Thus, through an axial movement of the operating handle 36 in the direction of the first end 25 of the housing 10, bolt 22 may be disengaged from the notch 21 due to the inclined position of the latter. For connecting the second shaft 2 with the second end 24 of the housing 10, the second shaft 2 may be equipped at its front end 13 with a peripheral groove 39, which may be disposed at the front end 13 of the shaft 2. In the engaged state, the bolt 22 may engage the groove 39, as a result of which the second shaft 2 may be fixed axially in the housing 10. For transferring the torque from the housing 10 to the second shaft 2, a cam 41 may be mounted in the borehole 40, which may accommodate the second shaft 2 and may be coaxial with the longitudinal axis 5. The cam 41 may be brought into engagement with a groove or a flattening 42 at the second shaft 2 and may, at least in part, protrude radially into the borehole 40. Furthermore, when the operating handle 36 is in the inoperative state, it may be held in the engaged position of the locking mechanism 23 by a spring 38, which may exert a compressive force from the housing 10 in the direction of the second shaft 2. For this purpose, a slide 37 may be inserted between the end of the spring 38, acting on the bolt 22.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. Various other modifications may be made by those skilled in the art which will embody the principles of the invention and fall within the spirit and the scope thereof.

The invention claimed is:

1. A device for limiting torque, comprising:
   first and second shafts having a longitudinal axis;
   at least first and second transfer elements arranged coaxial with the longitudinal axis of the first and second shafts, the first transfer element associated with the first shaft and the second transfer element associated with the second shaft;
   the two transfer elements having substantially complementary engaging faces;
   at least one elastic element configured to bias the engaging faces of the first and second transfer elements into engagement with each other;
   wherein an engaging face of the first transfer element has a first engageable contour, and an engaging face of the second transfer element has a second engageable contour, wherein first and second engageable contours each have first and second active angles and a first passive angle;
   wherein the first and second active angles of at least the first engageable contour are substantially unequal.

2. The device of claim 1, wherein the first active angle of the first engageable contour is substantially equal to the first passive angle of the first engageable contour.

3. The device of claim 1, wherein the first active angle of the first engageable contour is substantially unequal to the first passive angle of the first engageable contour.

4. The device of claim 1, wherein the first active angle of the first transfer element is acute with respect to the engaging face of the second transfer element.

5. The device of claim 1, wherein the first passive angle of the first transfer element is between about 45 and about 90 degrees with respect to the engaging face of the second transfer element.

6. The device of claim 1, wherein the first and second active angles of the first transfer element and the first passive angle of the first transfer element are 90 degrees or less with respect to the engaging face of the second transfer element.

7. The device of claim 1, wherein at least one engageable contour has a rounded-off portion.

8. The device of claim 7, the rounded-off portion having a radius, wherein the radius of the rounded-off portion is between about 0.1 mm and about 1.0 mm.

9. The device of claim 1, wherein the first engageable contour further comprises an apex, wherein the distance between the apex and the respective engaging face is between about 0.3 mm and about 2.0 mm.

10. The device of claim 1, wherein the at least one elastic element is a spring.

11. The device of claim 10, wherein the spring can be compressed to a pre-tensioned force of between about 500 N and about 2,500 N.

12. A device for limiting torque, comprising:
    first and second shafts having a longitudinal axis;
    at least first and second transfer elements arranged coaxial with the longitudinal axis of the first and second shafts, the first transfer element associated with the first shaft and the second transfer element associated with the second shaft;
    the two transfer elements having substantially complementary engaging faces;
    at least one elastic element configured to bias the engaging faces of the first and second transfer elements into engagement with each other;
    wherein an engaging face of the first transfer element has a first engageable contour, and an engaging face of the second transfer elements has a second engageable contour, wherein first and second engageable contours each have a first and second active angle and a first and second passive angle;
    wherein the first and second active angles of at least the first engageable contour are substantially unequal; and
    wherein the first and second passive angles of at least the first engageable contour are substantially unequal.

13. The device of claim 12, wherein the first active angle of the first engageable contour is substantially equal to the first passive angle of the first engageable contour.

14. The device of claim 12, wherein the first active angle of the first engageable contour is substantially unequal to the first passive angle of the first engageable contour.

15. The device of claim 12, wherein the first active angle of the first transfer element is acute with respect to the engaging face of the second transfer element.

16. The device of claim 12, wherein the first and second passive angles of the first transfer element are between about 45 and about 90 degrees with respect to the engaging face of the second transfer element.

17. The device of claim 12, wherein the first and second active angles of the first transfer element and the first and second passive angles of the first transfer element are 90 degrees or less with respect to the engaging face of the second transfer element.

18. The device of claim 12, wherein at least one engageable contour has a rounded-off portion.

19. The device of claim 18, the rounded-off portion having a radius, wherein the radius of the rounded-off portion is between about 0.1 mm and about 1.0 mm.

20. The device of claim 12, wherein the first engageable contour further comprises an apex, wherein the distance between the apex and the respective engaging face is between about 0.3 mm and about 2.0 mm.

21. The device of claim 12, wherein at least one elastic element is a spring.

22. The device of claim 21, wherein the spring can be compressed to a pre-tensioned force of between about 500 N and about 2,500 N.

* * * * *